United States Patent [19]

Giani et al.

[11] Patent Number: 4,849,422

[45] Date of Patent: Jul. 18, 1989

[54] PHARMACOLOGICALLY ACTIVE ALKYLOL DERIVATIVES

[75] Inventors: Roberto P. Giani, Locate Triulzi; Salvatore Malandrino, Cormano; Giancarlo Tonon, Milan, all of Italy

[73] Assignee: Dompe' Farmaceutici S.p.A., Milan, Italy

[21] Appl. No.: 4,028

[22] Filed: Jan. 16, 1987

[30] Foreign Application Priority Data

Jan. 20, 1986 [IT] Italy .................. 19121 A/86

[51] Int. Cl.$^4$ .................. C07D 401/04; C07D 403/04; A61K 31/495

[52] U.S. Cl. .................. 514/252; 540/596; 540/597; 540/598; 540/601; 544/238; 544/295; 544/357; 544/360; 544/365; 544/369; 544/379

[58] Field of Search .............. 544/305, 369, 360, 379, 544/295, 357, 238; 514/252

[56] References Cited

U.S. PATENT DOCUMENTS 4,064,244 12/1977 Sorg .................. 544/369

FOREIGN PATENT DOCUMENTS 94159 11/1983 European Pat. Off. ............ 544/365

OTHER PUBLICATIONS

A. Khundov, Khim Farm Zh 20 18 1986, Abstract only.

Primary Examiner—Robert Gerstl

Attorney, Agent, or Firm—Stevens, Davis, Miller & Mosher

[57] ABSTRACT

New alkylol derivatives are described, which belong to the class having the structure formula

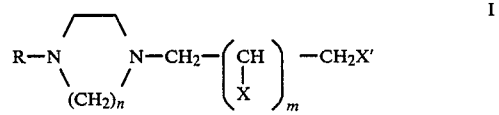

where
R represents a 5 or 6 membered heterocyclic ring selected among pyridine, pyrimidine, pyrazine, pyridazine, thiophene, furan, thiazole which optionally may be substituted with one or more groups selected among alkyl, alkoxy, halogen, amide, hydroxy, methylthio, trifluoromethyl, cyano, carboxy and the corresponding alkyl esters and salts with alkali metals
n is 2
X and X' represent each a hydrogen atom or hydroxy group with the exception of both being hydrogen atom, and X' may be hydroxyethoxy moiety
m is 0 or 1 and the corresponding non-toxic pharmaceutically acceptable acid addition salts. The compounds of the formula I are endowed with an interesting antitussive activity and, at their active dose, practically they are free of undesired side effects.

8 Claims, No Drawings

PHARMACOLOGICALLY ACTIVE ALKYLOL DERIVATIVES

The subject of the present invention relates to a new class of alkylol derivatives which show an interesting activity as antitussive agents.

More specifically the compounds of the invention are represented by alkylolpiperazine and alkylolhomopiperazine derivatives belonging to the general formula

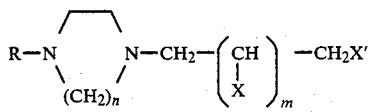

where
- R represents a 5 or 6 membered heterocyclic ring selected among pyridine, pyrimidine, pyrazine, pyridazine, thiophene, furan and thiazole which may be substituted with one or more groups selected among alkyl, trifluoromethyl, methylthio, alkoxy, halogen, amide, hydroxy, cyano, carboxy and the alkyl esters thereof
- n is 2
- X and X' represent each a hydrogen atom or hydroxy group with the exception of both being hydrogen atom, and X' may be hydroxyethoxy moiety
- m is 0 or 1.

The compounds of formula I display a marked antitussive activity and, at their active dose, practically they are free of the undesired side effects which generally are shown by the compounds on the market having analogous activity.

The process for preparing the compounds of formula I is essentially based on reacting a heterocyclic derivative R-Hal (II), where R has the above-cited meaning and Hal represents a halogen atom, preferably a chlorine atom, with a piperazine or homopiperazine alkylol derivative (III), in a suitable organic solvent at a temperature generally comprised between 60° and 130° C. The reaction can be schematically represented as following

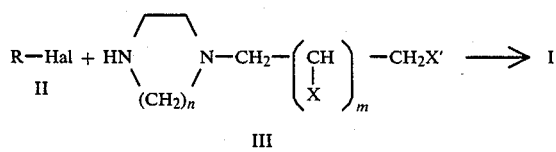

where the symbols R, Hal, n, m, X and X' have the above mentioned meaning.

The compounds I are isolated according to the known technique, in good yield and purity state.

The term alkyl or alkoxy is used through the description to mean an alkyl or alkoxy radical having from 1 to 3 carbon atoms respectively.

The term substituted hydroxy means a hydroxy means a hydroxy group substituted with an alkyl or with a hydroxyalkyl.

The compounds I, when the carboxy group is present and when desired, may be converted in a manner known per se into the corresponding alkali metal salts and they may be isolated as non-toxic addition salts with suitable acids.

For therapeutic administration, the compounds according to the present invention are used in the form of pharmaceutical preparation which contain said compounds in admixture with pharmaceutically acceptable carriers such as an organic or inorganic solid or liquid excipient suitable for oral or parenteral administration. The compounds of the invention may be contained in these pharmaceutical preparations in the form of free base or in the form of their non-toxic acid addition salts. The inorganic acids which may be employed to prepare these acid addition salts may be, for example, hydrochloric, hydrobromic, or sulphuric acid. The organic acids which may be employed are, for example, maleic, citric, fumaric and succinic acid. The pharmacuetical preparations may be in solid form as capsules, tablets, dragees or suppositories, or in liquid form such as solutions, suspensions or emulsions. If desired, there may be included in the above preparations auxiliary substances such as stabilizing agents and other commonly used additives, or there may be contained other therapeutically active agents suitable to be administered together with the compounds of the invention. While the dosage of the compounds will vary from the administration route and will also depend upon the age and condition of the patient, a dosage unit from about 1 to about 20 mg per kilogram of body weight per day, can be orally administered.

EXAMPLE 1

3-[4-(Pyrimidin-2-yl)piperazin-1-yl]propane-1,2-diol

Grams 3.2 of 1-(2,3-dihydroxypropyl)piperazine and 1.14 g of 2-chloropyrimidine in 50 ml dioxane were refluxed for two and a half hour. The reaction mixture was then settled and the solution evaporated to dryness. The residue obtained was extracted with hot acetone and filtered to remove all impurities. After resting 1.1 g of 3-[4-(pyrimidin-2-yl)piperazin-1-yl]propane-1,2-diol were separated, which melted at 118°-120° C.

Elementary analysis for $C_{11}H_{18}N_4O_2$

|  | C% | H% | N% |
|---|---|---|---|
| Calculated | 55.44 | 7.61 | 23.51 |
| Found | 55.40 | 7.70 | 23.48 |

EXAMPLE 2

3-[4-(6-Chloropyridazin-3-yl)piperazin-1-yl]propane-1,2-diol

Grams 32 of 1-(2,3-dihydroxypropyl)piperazine and 15 g of 3,6-dichloropyridazine in 700 ml isopropanol were refluxed for 24 hours. The reaction mixture was settled, the solid undissolvable removed and the solution evaporated to dryness. The so obtained residue was purified on column eluting with chloroform:methanol (9:1). Grams 2.1 of 3-[4-(6-chloropyridazin-3-yl)piperazin-1-yl]propane-1,2-diol, which, recrystallized from acetone, melted at 126°-128° C.

Elementary analysis for $C_{11}H_{17}Cl\ N_4O_2$

|  | C% | H% | N% |
|---|---|---|---|
| Calculated | 48.44 | 6.28 | 20.54 |
| Found | 48.62 | 6.31 | 20.53 |

EXAMPLE 3

2-[4-(2,3-Dihydroxypropyl)piperizin-1-yl]nicotinamide

Operation was carried out in a manner similar to the one described in Example 2, using 1.6 g of 2-chloronicotinamide, 3.2 g of 1-(2,3-dihydroxypropyl)-piperazine and 30 ml ethanol and refluxing overnight. Column purification of the residue gave 1 g of 2-[4-(2,3-dihydroxypropyl)piperazin-1-yl]nicotinamide, which, recrystallized from acetone, melted at 140°–142° C.

Elementary analysis for $C_{13}H_{20}N_4O_3$

|  | C% | H% | N% |
|---|---|---|---|
| Calculated | 55.70 | 7.19 | 19.99 |
| Found | 55.77 | 7.11 | 20.04 |

EXAMPLE 4

3-[4-(Pyridin-2-yl)piperazin-1-yl]propane-1,2-diol dihydrochloride

Operation was carried out in a manner similar to the one previously described, using 2-chloropyridine and 1-(2,3-dihydroxypropyl) piperazine. The residue obtained after evaporation to dryness was dissolved in a small amount of concentrated hydrochloric acid and diluted with isopropanol. After resting, 3-[4-(pyridin-2-yl) piperazin-1-yl]propane-1,2-diol dihydrochloride melting at 238°–242° C., was obtained with the 53.6% yield.

Elementary analysis for $C_{12}H_{19}N_3O_2 \cdot 2HCl$

|  | C% | H% | N% |
|---|---|---|---|
| Calculated | 46.46 | 6.82 | 13.54 |
| Found | 46.41 | 6.89 | 13.48 |

EXAMPLE 5

2-[4-(2,3-Dihydroxypropyl)piperazin-1-yl]nicotinic acid

Grams 32 of 1-(2,3-dihydroxypropyl)piperazine and 15.7 g of 2-chloronicotinic acid in 500 ml dioxane were refluxed for 8 hours. The reaction mixture was cooled, settled, the solvent separated and removed. The residue was triturated under heating with absolute ethanol and gave 16.2 g of 2-[4-(2,3-dihydroxypropyl)piperazin-1-yl]nicotinic acid melting at 210°–212° C. (with decomposition)

Elementary analysis for $C_{13}H_{19}N_3O_4$

|  | C% | H% | N% |
|---|---|---|---|
| Calculated | 55.50 | 6.81 | 14.94 |
| Found | 55.51 | 6.88 | 15.02 |

EXAMPLE 6

6-[4-(2,3-Dihydroxypropyl)piperazin-1-yl]nicotinic acid

Operation was carried out in a manner similar to the one previously described in Example 5, using 1.6 g of 6-chloronicotinic acid and 3.2 g of 1-(2,3-dihydroxypropyl)piperazine in 50 ml dioxane. Grams 1.95 of 6-[4-(2,3-dihydroxypropyl)piperazin-1-yl]nicotinic acid were obtained, which, recrystallized from hot water, melted at 244°–246° C. (with decomposition).

Elementary analysis for $C_{13}H_{19}N_3O_4$

|  | C% | H% | N% |
|---|---|---|---|
| Calculated | 55.50 | 6.81 | 14.94 |
| Found | 55.60 | 6.80 | 14.91 |

EXAMPLE 7

2-[4-(2-Hydroxyethyl)piperazin-1-yl]nicotinic acid

Operation was carried out in a manner similar to the one previously described in Example 5, using 10.4 g of 1-(2-hydroxyethyl)piperazine and 6.3 g of 2-chloronicotinic acid in 100 ml dioxane under reflux for 18 hours. Grams 3.9 of 2-[4-(2-hydroxyethyl)piperazin-1-yl]nicotinic acid, melting at 148°–171° C. (with decomposition), were obtained.

Elementary analysis for $C_{12}H_{17}N_3O_3$

|  | C% | H% | N% |
|---|---|---|---|
| Calculated | 57.36 | 6.82 | 16.72 |
| Found | 57.28 | 6.78 | 16.80 |

EXAMPLE 8

2-[4-(2,3-Dihydroxypropyl)homopiperazin-1-yl]nicotinic acid

Grams 5 of 1-(2,3-dihydroxypropyl)homopiperazine and 2.25 g of 2-chloronicotinic acid in 50 ml dioxane were refluxed for 24 hours. The reaction mixture was evaporated to dryness and the residue was purified on column eluting with ethanol:ammonium hydroxyde (95:5). The fractions containing the product were dried and the residue, triturated with acetonitrile, gave 1.3 g of 2-[4-(2,3-dihydroxypropyl)homopiperazin-1-yl]nicotinic acid, melting at 70°–77° C. (with decomposition).

Elementary analysis for $C_{14}H_{21}N_3O_4$

|  | C% | H% | N% |
|---|---|---|---|
| Calculated | 56.93 | 7.17 | 14.23 |
| Found | 57.01 | 7.17 | 14.24 |

EXAMPLE 9

2-[4-(3-Hydroxypropyl)piperazin-1-yl]nicotinic acid

Grams 8.65 of 1-(3-hydroxypropyl)piperazine and 4.7 g of 2-chloronicotinic acid in 100 ml dioxane were refluxed for 6 hours. The reaction mixture was cooled and settled. The residual oil, crystallized from 95° ethanol, gave 2.3 g of 2-[4-(3-hydroxypropyl)piperazin-1-yl]nicotinic acid, melting at 222°–225° C. (with decomposition).

Elementary analysis for $C_{13}H_{19}N_3O_3$

|  | C% | H% | N% |
|---|---|---|---|
| Calculated | 58.85 | 7.22 | 15.84 |
| Found | 58.91 | 7.21 | 15.80 |

EXAMPLE 10

3-[4-(Cyanopyridazin-3-yl)piperazin-1-yl]propane-1,2-diol dihydrochloride

Grams 6.9 of 1-(2,3-dihydroxypropyl)piperazine and 3.0 g of 4-cyano-3-chloropyridazine in 60 ml dioxane were refluxed for 2 hours. The reaction mixture was settled, the supernatant liquor evaporated to dryness and the residue, which formed, was dissolved in 10 ml concentrated hydrochloric acid and diluted with 10 volumes of isopropanol. A precipitate was obtained formed by a gummy oil, which solidified afterwards giving 5.9 g of 3-[4-(4-cyanopyridazin-3-yl)piperazin-1yl]propane-1,2-diol dihydrochloride which melted at 128°–130° C.

Elementary analysis for $C_{12}H_{17}N_5O_2 \cdot 2HCl$

|  | C% | H% | N% |
|---|---|---|---|
| Calculated | 42.87 | 5.69 | 20.83 |
| Found | 42.78 | 5.65 | 20.88 |

EXAMPLE 11

4-[4-(2,3-Dihydroxypropyl)piperazin-1-yl]pyrimidine-5-carboxylic acid ethyl ester dihydrochloride Grams 7.4 of 1-(2,3-dihydroxypropyl)piperazine and 4.3 g of 4-chloropyrimidine-5-carboxylic acid ethyl ester were warmed to 90° C. for 45 minutes in 100 ml dioxane. The reaction mixture was then settled, the supernatant liquor evaporated to dryness and the residue dissolved in hydrochloric ethanol and diluted with isopropanol until complete precipitation. By addition of 95° ethanol, the so formed gum crystallized and 4 g of 4-[4-(2,3-dihydroxypropyl)piperazin-1-yl]pyrimidine-5-carboxylic acid ethyl ester dihydrochloride, melting at 190°–193° C. (with decomposition), were obtained.

Elementary analysis for $C_{14}H_{22}N_4O_4 \cdot 2HCl$

|  | C% | H% | N% |
|---|---|---|---|
| Calculated | 43.87 | 6.31 | 14.62 |
| Found | 43.79 | 6.30 | 14.62 |

EXAMPLE 12

4-[4-(2,3-Dihydroxypropyl)piperazin-1-yl]pyrimidine-5-carboxylic acid sodium salt Grams 2 of 4-[4-(2,3-dihydroxypropyl)piperazin-1-yl]pyrimidine-5 carboxylic acid ethyl ester dihydrochloride, obtained in Example 11, were treated with 0.62 g sodium hydroxide in 20 ml water at 70° C. for 15 minutes. Then it was cooled and evaporated to dryness, the residue taken up with absolute ethanol, filtered and the undissolvable removed. The clear filtrate was concentrated to a 10 ml volume and allowed to rest. Grams 0.5 of 4-[4-(2,3-dihydroxypropyl)piperazin-1-yl]pyrimidine-5-carboxylic acid sodium salt melting at 268°–273° C. (with decomposition) were obtained.

Elementary analysis for $C_{12}H_{17}N_4NaO_4$

|  | C% | H% | N% |
|---|---|---|---|
| Calculated | 47.37 | 5.63 | 18.41 |
| Found | 47.42 | 5.60 | 18.35 |

EXAMPLE 13

3-[4-(2,3-Dihydroxypropyl)piperazin-1-yl]pyridazine-4-carboxylic acid ethyl ester Grams 10.2 of 1-(2,3-dihydroxypropyl)piperazine and 5.9 g of 3-chloropyridazine-4-carboxylic acid ethyl ester in 100 ml dioxane were refluxed for one hour. Then it was settled, the solvent evaporated till dryness, and the residue dissolved in chloroform and washed with a small amount of water. The organic phase was made anhydrous, evaporated to dryness and the residue, purified on a column eluting with chloroform:methanol (9:1), gave 2.4 g of 3-[4-(2,3-dihydroxypropyl)piperazin-1-yl]pyridazine-4-carboxylic acid ethyl ester as an oil.

Elementary analysis for $C_{14}H_{22}N_4O_4$

|  | C% | H% | N% |
|---|---|---|---|
| Calculated | 54.18 | 7.14 | 18.05 |
| Found | 54.09 | 7.15 | 17.98 |

EXAMPLE 14

2-[4-(2-Hydroxypropyl)piperazin-1-yl]nicotinic acid

Grams 3 of 1-(2-hydroxypropyl)piperazine and 1.6 g of 2-chloronicotinic acid in 50 ml dioxane were refluxed for 2 days. The react ion mixture was cooled, then allowed to rest for 2 days, the solvent was removed and the residue was crystallized from absolute ethanol to give 1.2 g of 2-[4-(2-hydroxypropyl)piperazin-1-yl]nicotinic acid, melting at 222°–223° C. (with decomposition).

Elementary analysis for $C_{13}H_{19}N_3O_3$

|  | C% | H% | N% |
|---|---|---|---|
| Calculated | 58.85 | 7.22 | 15.84 |
| Found | 58.92 | 7.31 | 19.87 |

EXAMPLE 15

2-{4-[2-(2-Hydroxyethoxy)ethyl]piperazin-1-yl}nicotinic acid

Grams 5.9 of 1-(2-hydroxyethoxyethyl)piperazine and 2.7 g of 2-chloronicotinic acid in 50 ml dioxane were refluxed for 3 days. The reaction mixture was then cooled and allowed to rest for 2 days, afterwards the solvent was removed and the residue crystallized from absolute ethanol, gave 1.1 g of 2-{4-[2-(2-hydroxy ethoxy)ethyl]piperazin-1-yl}nicotinic acid melting at 172°–174° C.

Elementary analysis for $C_{14}H_{21}N_3O_4$

|  | C% | H% | N% |
|---|---|---|---|
| Calculated | 56.93 | 7.17 | 14.23 |
| Found | 56.87 | 7.21 | 14.18 |

EXAMPLE 16

3-[4-(3-Hydroxypyridin-2-yl)piperazin-1-yl]propane-1,2-diol dihydrochloride

Grams 6.4 of 1-(2,3-dihydroxypropyl)piperazine and 3.5 g of 2-bromo-3-hydroxypyridine in 70 ml cyclohexanol were refluxed for 24 hours, then the solvent was distilled off and the obtained residue was purified on column eluting with chloroform:methanol (9:1). The obtained product was dissolved in concentrated hydrochloric acid and diluted with isopropanol until incipient precipitation. After resting, were obtained 1.5 g of 3-[4-(3-hydroxypyridin-2-yl)piperazin-1-yl]propane-1,2-diol dihydrochloride melting at 243°–247° C. (with decomposition).

Elementary analysis for $C_{12}H_{19}N_3O_3 \cdot 2HCl$

|  | C% | H% | N% |
|---|---|---|---|
| Calculated | 44.18 | 6.49 | 12.88 |
| Found | 44.27 | 6.57 | 12.74 |

EXAMPLE 17

2-Methylthio-4-[4-(2,3-dihydroxypropyl)piperazin-1-yl]pyrimidine-5-carboxylic acid ethyl ester Grams 4.6 of 2-methylthio-4-chloropyrimidine-5-carboxylic acid ethyl ester and 6.4 g of 1-(2,3-dihydroxypropyl)piperazine in 50 ml dioxane were refluxed for 30 minutes. The mixture was cooled and settled, then the solvent was evaporated and the dried residue purified on column eluting with chloroform:methanol (9:1). Grams 4.8 of 2-methylthio-4-[4-(2,3-dihydroxypropyl)-piperazin-1-yl]pyrimidine-5-carboxylic acid ethyl ester as an oil, were obtained.

Elementary analysis for $C_{15}H_{24}N_4O_4S$

|  | C% | H% | N% |
|---|---|---|---|
| Calculated | 50.54 | 6.78 | 15.72 |
| Found | 50.65 | 6.82 | 15.64 |

EXAMPLE 18

3-[4-(2,3-Dihydroxypropyl)piperazin-1-yl]pyrazine-2-carboxylic acid methyl ester dihydrochloride Grams 20.5 of 1-(2,3-dihydroxypropyl)piperazine and 11 g of 3-chloropyrazine-2-carboxylic acid methyl ester in 100 ml dioxane were refluxed for one hour. The reaction mixture was cooled and settled, the solvent evaporated and the obtained residue dissolved in concentrated hydrochloric acid and the solution diluted with isopropanol until incipient precipitation. After resting, 12.7 g of 3-[4-(2,3-dihydroxypropyl)piperazin-1-yl]pyrazine-2-carboxylic acid methyl ester dihydrochloride melting at 195°–197° C. (with decomposition), were obtained.

Elementary analysis for $C_{13}H_{20}N_4O_4 \cdot 2HCl$

|  | C% | H% | N% |
|---|---|---|---|
| Calculated | 42.29 | 6.00 | 15.17 |
| Found | 42.35 | 5.95 | 15.14 |

EXAMPLE 19

3-[4-(2,3-Dihydroxypropyl)piperazin-1-yl]pyrazine-2-carboxylic acid sodium salt

Grams 5 of 3-[4-(2,3-dihydroxypropyl)piperazin-1-yl]pyrazine-2-carboxylic acid methyl ester, obtained as in Example 18, were dissolved in a sodium bicarbonate aqueous saturated solution. The solution was extracted three times with 100 ml chloroform and the organic phases collected together were evaporated to dryness to give 4 g of 3-[4-(2,3-dihydroxypropyl)piperazin-1-yl]pyrazine-2-carboxylic acid, which were dissolved in 40 ml water and 0.5 g sodium hydroxyde and refluxed for 8 hours. The reaction mixture was evaporated to dryness and the residue taken up several times with absolute ethanol, each time distilling to dryness. The residue obtained from distillation was triturated with diethyl ether and gave 2.7 g of 3-[4-(2,3-dihydroxypropyl)piperazin-1-yl]pyrazine-2-carboxylic acid, sodium salt, melting at 175°–184° C.

Elementary analysis for $C_{12}H_{17}Na\,N_4O_4$

|  | C% | H% | N% |
|---|---|---|---|
| Calculated | 47.37 | 5.63 | 18.41 |
| Found | 47.41 | 5.62 | 18.38 |

EXAMPLE 20

3-[4-(1,3-Thiazol-2-yl)piperazin-1-yl]propane-1,2-diol

Grams 6.4 of 1-(2,3-dihydroxypropyl)piperazine and 3.3 g of 2-bromo-1,3-thiazole in 50 ml dioxane were refluxed for 24 hours. The reaction mixture was evaporated to dryness and the so obtained residue was purified on column eluting with chloroform:methanol (9:1). Grams 1.5 of 3-[4-(1,3-thiazol-2-yl)piperazin-1-yl] propane-1,2-diol which, by recrystallization from acetone, melted at 138°–139° C., were obtained.

Elementary analysis for $C_{10}H_{17}N_3O_2S$

|  | C% | H% | N% |
|---|---|---|---|
| Calculated | 49.36 | 7.04 | 17.27 |
| Found | 49.48 | 6.98 | 17.37 |

EXAMPLES 21–25

The following listed compounds have been prepared from the corresponding suitable reactants, according to the previously described method:

2-[4-(2,3-Dihydroxypropyl)piperazin-1-yl]thiophene-3-carboxylic acid methyl ester.
3-[4-(Pyrazin-2-yl)piperazin-1-yl]propane-1,2-diol.
3-[4-(6-Methoxypyridazin-3-yl)piperazin-1-yl]propane-1,2-diol.
3-[4-(Thiophen-2-yl)piperazin-1-yl]propane-1,2-diol.
2-[4-(2,3-Dihydroxypropyl)piperazin-1-yl]furan-5-carboxylic acid.

The antitussive activity of the compounds of the invention has been evaluated using as comparison compounds both dropropizine, which represents the antitussive compound having the closest chemical structure analogy with the compounds of the invention, and codeine. The compounds of the invention, compared to the standard at the same dose, showed to be endowed with a higher or comparable activity and to be practically devoided of undesired side effects. Thus, besides the tests able to evaluate the antitussive activity, also tests for determining the effect on the sleeping time interval induced by barbiturate administration were carried out. Tests were performed on the compounds of formula I according to the methods herebelow reported and gave the results listed in Tables 1 and 2.

Effect on cough induced by citric acid aerosol in guinea pig

The method described by R. W. Pickering and G. W. L. James (Arzneim. Forsch./Drug Res., 29 (I), No. 2, 1979) slightly modified, was followed. The animals were placed in a perspex box having the size 20×14×12 cm, and were exposed to an aerosol of 5% p/v citric acid in distilled water. The aerosol was prepared by bubbling 0.5 atm compressed air through a nebulizer containing 4–5 ml of the citric acid solution; the animals were exposed for 5 minutes counting the number of short coughs during this period. The compounds under examination were orally administered one hour before the tussive stimulus.

The animals were selected the day before and allowed to the test only if they showed a number of short coughs equal or higher than 10.

The results are given in the following Table 1.

TABLE 1

| Compound | Dose mg/Kg p.o. | Inhibition % | p* |
|---|---|---|---|
| Codeine | 100 | 63.17 | <0.001 |
| Dropropizine(±) | 100 | 48.57 | <0.01 |
| Example 1 | 100 | 42.80 | <0.01 |
| Example 2 | 100 | 29.95 | <0.02 |
| Example 3 | 100 | 51.66 | <0.01 |
| Example 4 | 100 | 29.80 | <0.02 |
| Example 5 | 100 | 64.01 | <0.001 |
| Example 6 | 100 | 45.15 | <0.01 |
| Example 7 | 100 | 46.61 | <0.01 |
| Example 8 | 100 | 60.00 | <0.001 |

*"t" of Student for paired data.

Effect on the sleeping time interval induced by barbiturates in mice

The sleep was induced by intraperitoneal administration of 40 mg/Kg pentobarbital sodium. The narcosis start was considered from the moment when the animal, lying on its back, lost its straightening reflex. The narcosis end was considered from the moment when the animal recovered such reflex. (Turner R. in "Screening Methods in Pharmacology", Academic Press, 6, 70, 1985).

The compounds under examination were orally administered 1 hour before the barbiturate administration; to the control animals 10 ml/Kg tap water were administered.

The results are listed in the following Table 2.

TABLE 2

| Compound | Dose mg/Kg p.o. | Δ % | p* |
|---|---|---|---|
| Codeine | 100 | +122.56 | <0.001 |
| Dropropizine (±) | 100 | +153.80 | <0.001 |
| Example 1 | 100 | +35.12 | <0.05 |
| Example 2 | 100 | +3.03 | NS |

TABLE 2-continued

| Compound | Dose mg/Kg p.o. | Δ % | p* |
|---|---|---|---|
| Example 3 | 100 | +13.42 | |
| Example 4 | 100 | −3.58 | NS |
| Example 5 | 100 | −10.23 | NS |
| Example 6 | 100 | +1.22 | NS |
| Example 7 | 100 | −3.06 | NS |
| Example 8 | 100 | −12.80 | NS |

*"t" of Student
NS not significant

What we claim is:

1. Alkylolpiperazines of the formula

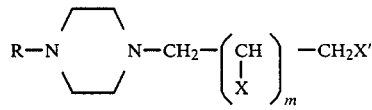

wherein
R represents a 5 or 6 membered heterocyclic ring selected from the group consisting of pyridine, pyrimidine, pyrazine, pyridazine, thiophene, and furan which may be optionally substituted with one or more members selected from the group consisting of a 1–3 carbon atom alkyl, trifluoromethyl, methylthio, a 1–3 carbon atom alkoxy, halogen, amide, hydroxy, cyano and carboxy and the corresponding alkyl esters and salts with alkali metals,
m is 1,
X and X' each represent a hydroxy group and X' may also be a hydroxyethoxy moiety,
and the corresponding non-toxic pharmaceutically acceptable acid addition salts.

2. Alkylolpiperazines according to claim 1, characterized in that R is an optionally substituted pyridin-2-yl radical.

3. 2-[4-(2,3-Dihydroxypropyl)piperazin-1-yl]nicotinic acid.

4. 3-[4-(6-Chloropyridazin-3-yl)piperazin-1-yl]propane-1,2-diol.

5. 2-[4-(2,3-Dihydroxypropyl)piperazin-1-yl]nicotinamide.

6. 6-[4-(2,3-Dihydroxypropyl)piperazin-1-yl]nicotinic acid.

7. A pharmaceutical composition for the treatment of coughs containing an antitussively effective amount of a compound according to any one of claims 1, 2, 3, 4, 5 or 6 in admixture with one or more pharmaceutically acceptable excipients.

8. A method of treating a patient suffering from cough, which comprises administering to said patient an antitussively effective amount of a compound according to any one of claims 1, 2, 3, 4, 5 or 6.

* * * * *

UNITED STATES PATENT AND TRADEMARK OFFICE
CERTIFICATE OF CORRECTION

PATENT NO. : 4,849,422

DATED : JULY 18, 1989

INVENTOR(S) : ROBERTO P. GIANI; SALVATORE MALANDRINO; GIANCARLO TONON

It is certified that error appears in the above-identified patent and that said Letters Patent is hereby corrected as shown below:

COLUMN 1, LINE 61, Delete "means a hydroxy".

COLUMN 5, LINE 2, Change "(Cyanopyridazin" to -- (4-Cyanopyridazin --;

LINE 14, Change "lyl" to -- 1-yl --.

COLUMN 6, LINE 28, Change "react ion" to -- reaction --.

Signed and Sealed this

First Day of January, 1991

Attest:

HARRY F. MANBECK, JR.

*Attesting Officer*     *Commissioner of Patents and Trademarks*